United States Patent
Haflinger et al.

(10) Patent No.: US 9,734,690 B2
(45) Date of Patent: Aug. 15, 2017

(54) SYSTEM AND METHOD FOR ACTIVITY MONITORING AND FALL DETECTION

(71) Applicant: Nortek Security & Control LLC, Carlsbad, CA (US)

(72) Inventors: James J Haflinger, Carlsbad, CA (US); Jeffrey Michael Sweeney, Carlsbad, CA (US)

(73) Assignee: Nortek Security & Controls LLC, Carlsbad, CA (US)

( * ) Notice: Subject to any disclaimer, the term of this patent is extended or adjusted under 35 U.S.C. 154(b) by 0 days.

(21) Appl. No.: 15/130,405

(22) Filed: Apr. 15, 2016

(65) Prior Publication Data

US 2016/0307427 A1    Oct. 20, 2016

Related U.S. Application Data

(60) Provisional application No. 62/147,779, filed on Apr. 15, 2015.

(51) Int. Cl.
*G08B 21/04* (2006.01)
*G08B 25/08* (2006.01)
*A61B 5/00* (2006.01)

(52) U.S. Cl.
CPC ........ *G08B 21/0446* (2013.01); *A61B 5/0022* (2013.01); *A61B 5/6822* (2013.01); *G08B 21/043* (2013.01); *G08B 25/08* (2013.01); *A61B 2562/0219* (2013.01)

(58) Field of Classification Search
CPC .... A61B 5/1117; G08B 21/0446; H04L 67/22
See application file for complete search history.

(56) References Cited

U.S. PATENT DOCUMENTS

| | | |
|---|---|---|
| 6,307,481 B1 | 10/2001 | Lehrman et al. |
| 6,501,386 B2 | 12/2002 | Lehrman et al. |
| 6,703,939 B2 | 3/2004 | Lehrman et al. |
| 6,864,796 B2 | 3/2005 | Lehrman et al. |
| 7,095,331 B2 | 8/2006 | Lehrman et al. |
| 7,123,141 B2 | 10/2006 | Contestabile |
| 7,126,472 B2 | 10/2006 | Kraus et al. |
| 7,141,026 B2 | 11/2006 | Aminian et al. |

(Continued)

FOREIGN PATENT DOCUMENTS

| | | |
|---|---|---|
| EP | 1643779 A1 | 4/2006 |
| EP | 2040441 A1 | 3/2009 |

(Continued)

*Primary Examiner* — Curtis Odom
(74) *Attorney, Agent, or Firm* — Schwegman Lundberg & Woessner, P.A.

(57) ABSTRACT

Devices and methods of using a personal emergency reporting system device is described. The personal emergency reporting system (PERS) device wakes up based on timing, manual activation or an accelerometer in the PERS device detecting an abnormal condition. The PERS device measures the orientation and correlate and sends statistics to a console. The PERS device determines whether a predetermined threshold has been met to determine whether a fall event has occurred or whether to enter a more active monitoring state. The PERS device also determines whether it is appropriate to transmit an alarm to a central monitoring station via the console and transmits the alarm if desired.

20 Claims, 4 Drawing Sheets

(56) References Cited

U.S. PATENT DOCUMENTS

| | | |
|---|---|---|
| 7,145,461 B2 | 12/2006 | Lehrman et al. |
| 7,444,167 B2 | 10/2008 | Chang et al. |
| 7,479,890 B2 | 1/2009 | Lehrman et al. |
| 7,652,569 B2 | 1/2010 | Kiff et al. |
| 7,865,150 B2 | 1/2011 | McFarland et al. |
| 7,907,931 B2 | 3/2011 | Hartigan et al. |
| 7,962,308 B2 | 6/2011 | Makino |
| 8,116,724 B2 | 2/2012 | Peabody |
| 8,275,352 B2 | 9/2012 | Forstall et al. |
| 8,447,265 B2 | 5/2013 | Flippo et al. |
| 8,684,922 B2 | 4/2014 | Tran |
| 2003/0027547 A1 | 2/2003 | Wade |
| 2010/0099410 A1 | 4/2010 | Sweeney et al. |
| 2012/0101770 A1* | 4/2012 | Grabiner ............... A61B 5/1116 702/141 |
| 2012/0157032 A1 | 6/2012 | Goodman |
| 2014/0077946 A1 | 3/2014 | Tran |
| 2014/0155705 A1 | 6/2014 | Papadopoulos et al. |
| 2014/0266787 A1 | 9/2014 | Tran |
| 2014/0375461 A1* | 12/2014 | Richardson ........ G08B 21/0446 340/573.7 |

FOREIGN PATENT DOCUMENTS

| | | |
|---|---|---|
| EP | 2510675 A1 | 10/2012 |
| EP | 2541998 A1 | 1/2013 |

\* cited by examiner

SYSTEM AND METHOD FOR ACTIVITY MONITORING AND FALL DETECTION

PRIORITY CLAIM

This application claims the benefit of priority to U.S. Provisional Patent Application Ser. No. 62/147,779, filed Apr. 15, 2015, and entitled "SYSTEM AND METHOD FOR ACTIVITY MONITORING AND FALL DETECTION," which is incorporated herein by reference in its entirety.

TECHNICAL FIELD

Embodiments pertain to individual safety. Some embodiments relate to detection of individual falls and subsequent activity monitoring.

BACKGROUND

With the improvement in longevity due to medical advances and care, a corresponding increase has occurred in the elderly and disabled population. Whether these individuals are in a hospice or assisted living community or living at home, there is a constant need to closely monitor the physical condition of each individual as even when a caregiver is available, the caregiver is not present at all times. Even relatively minor physical accidents may result in catastrophic injuries given the frailty of these individuals, and may be aggravated given the delay in determining that the individual has suffered a fall that has caused injury. For many, the risk of injury from falling, as well as the frequency of falls, increases with age. Falls of elderly individuals are a leading cause of injury and death. Serious injury, such as hip fractures and head trauma, caused by a fall may prevent an individual from contacting or a caregiver or medical personnel, thereby exacerbating the injuries suffered.

BRIEF DESCRIPTION OF THE FIGURES

In the figures, which are not necessarily drawn to scale, like numerals may describe similar components in different views. Like numerals having different letter suffixes may represent different instances of similar components. The figures illustrate generally, by way of example, but not by way of limitation, various embodiments discussed in the present document.

DETAILED DESCRIPTION

The following description and the drawings sufficiently illustrate specific embodiments to enable those skilled in the art to practice them. Other embodiments may incorporate structural, logical, electrical, process, and other changes. Portions and features of some embodiments may be included in, or substituted for, those of other embodiments. Embodiments set forth in the claims encompass all available equivalents of those claims.

While personal emergency reporting system (PERS) devices (sometimes referred to as personal emergency response system devices) can be used to aid in fall detection, such devices may suffer from various problems. For example, current personal emergency reporting system devices may have embedded accelerometers that determine a fall event using acceleration processed using local firmware. The use of acceleration increasing the sensitivity of detection that uses shock thresholds (sudden de-accelerations) at the cost of increasing the number of false alerts due to the increased sensitivity. The use of accelerometers may provide benefits in power consumption and provide a reasonable battery life. Upon determining that a fall event has likely occurred, the device may automatically initiate and transmit an alarm to a monitoring station. A combination of acceleration and shock thresholds may help to alleviate the number of false alerts but may still engender certain issues. To this end, in general orientation of the personal emergency reporting system device may be used instead of, or in addition to, the use of acceleration and/or shock thresholds, hereinafter also referred to as the physical characteristics of the current personal emergency reporting system device. In some embodiments, the personal emergency reporting system device may use acceleration and/or shock thresholds to wake up the personal emergency reporting system device for subsequent orientation (and perhaps biometric) measurements to determine a fall event but may not be used to actually determine the fall event. The personal emergency reporting system device may, as indicated in more detail below, also take into account changes in biometrics of the user.

Due to limited processor and communication nature of the devices, the algorithm used to determine whether or not a fall event has occurred may be programmed into the device and may in some cases be unable to be altered. An algorithm that is too sensitive triggers false alerts, resulting in annoying end users and creating commercial problems and potential problems for emergency service providers. An algorithm that is not sensitive enough may not detect real falls, with the corresponding and liability issues of greater concern. It would be desirable to provide a device that is able to detect falls and monitor for subsequent activity in a power-sensitive manner. In some embodiments, the algorithm may use orientation alone, or orientation and biometric measurements, to determine whether a fall event has occurred. In other embodiments, the algorithm may balance between acceleration, shock threshold and orientation to determine whether a fall event has occurred. In some embodiments, the algorithm may be personalized based on historical orientation and/or biometric thresholds of the user. The historical thresholds may be, for example, downloaded from a previous personal emergency reporting system device associated with the user or determined by a training session with the user when the personal emergency reporting system device is initially obtained. In some embodiments, the personal emergency reporting system device monitors false alerts and determines when the false alert rate (i.e., the number of false alerts within a false alert time period) exceeds a false alert threshold that a different user is wearing the personal emergency reporting system device.

Figure 1:
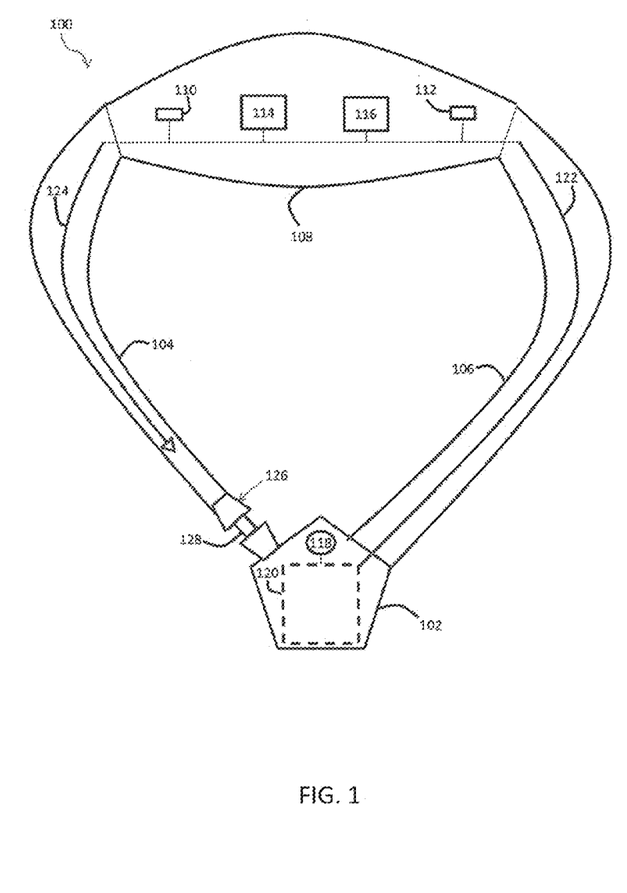
FIG. 1 illustrates a motion sensing necklace in accordance with some embodiments.

In more detail, false positive fall alerts may be a significant problem with personal emergency reporting systems. Personal emergency reporting system device devices may be provided in one or more locations. While other locations may be more desirable from a purely functional standpoint, a personal emergency reporting system that is incorporated into a necklace-type design may be the most practical from a user standpoint to permit various functionality. Other locations may include the personal emergency reporting system being incorporated in a belt, wristband, armband, leg band, eyewear or in clothing of the wearer. One such personal emergency reporting system, which incorporates fall detection and detection of subsequent motion, is shown and described herein. The fall detection apparatus, as shown in FIG. 1, is embedded within a pendant and configured to be worn around an individual's neck. In such an arrangement, care may be taken to minimize the probability of a false positive fall detection due to movement of the pendant during normal activities such as walking and transitions between various body positions, as well as inadvertent contact of the pendant with an object, which may generate a false positive fall detection. Moreover, when coupled with movement and activity monitoring immediately afterward, the rate of false positive fall detection may be decreased.

One embodiment of a personal emergency reporting system in the form of a fall and motion detection necklace is illustrated in FIG. 1. Necklace 100 includes a pendant 102 that is attached to lower ends of first and second lanyards 104, 106. A neck strap 108 is attached to the upper ends of lanyards 104, 106. When necklace 100 is worn, neck strap 108 rests against the user's neck while pendant 102 is suspended and hangs below the neck by lanyards 104, 106.

Neck strap 108 houses two or more sensors 110 and 112. Sensors 110 and 112 may be, for example, accelerometers, gyroscopes, magnetometers, altimeters or combinations of these or other components for detecting motion, including linear acceleration and pendant orientation. In one embodiment, sensors 110 and 112 may be three axis accelerometers, capable of detecting motion in the x, y and z planes. As shown in FIG. 1, sensors 110 and 112 are positioned within opposing sides of neck strap 108, such that they are located on opposing and offsetting sides of the neck region or near the upper region of the collar bone. The sensors 110 and 112 may be symmetric or offset. Microprocessor 114 (and memory) is also located in neck strap 108 and processes signals from sensors 110 and 112 to determine whether a fall event and/or motion has occurred. Microprocessor 114 is configured (e.g., programmed) to operate in the specified manner or to perform part or all of any operation described herein. Microprocessor 114 is configured using software stored in the memory such that the instructions contained in the software exist in a statutory, non-transitory, machine readable medium form when being stored and implemented by circuitry in microprocessor 114. Although not shown, the memory may contain any or all of removable storage and non-removable storage, volatile memory or non-volatile memory. The term "machine readable medium" may include any medium that is capable of storing, encoding, or carrying instructions for execution by microprocessor 114 and that cause microprocessor 114 to perform any one or more of the techniques of the present disclosure, or that is capable of storing, encoding or carrying data structures used by or associated with such instructions. Non-limiting machine readable medium examples may include solid-state memories such as semiconductor memory devices (e.g., Electrically Programmable Read-Only Memory (EPROM), Electrically Erasable Programmable Read-Only Memory (EEPROM)) and flash memory devices.

RF transmitter 116, also located in neck strap 108, transmits fall detection alarms and other motion detection signals generated by microprocessor 114 via antenna 124 to a personal emergency reporting system home console (not shown) that is local to the user. Alternatively, transmitter 116 may be a transceiver, for example, to provide the ability to update the firmware or algorithm on the necklace 100. The communication equipment in necklace 100 includes transmit and receive chains that each includes power amplifiers, modulators, buffers, mixers, filters and isolators, among other components. That is, a receiver may be provided in addition to transmitter 116. In one embodiment, as sensors 110 and 112 are located at opposing ends of neck strap 108, processor 114 and transmitter 116 are located between sensors 110 and 112.

Turning back to FIG. 1, neck strap 108 is in the form of a casing that is hardened to protect its internal electronics, and that is contoured so as to fit comfortably around the user's neck. In addition, neck strap 108 is configured to be sufficiently broad to house the system electronics, which also provides increased stability for motion sensing.

Figure 2:
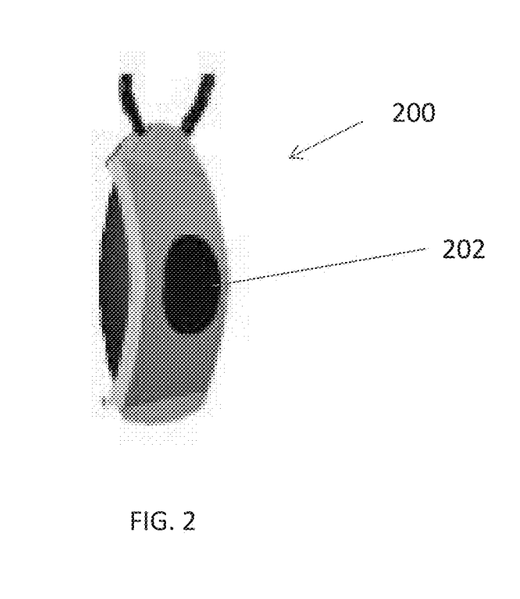
FIG. 2 illustrates a personal emergency reporting system device in accordance with some embodiments.

Pendant 102 is attached to the lower ends of lanyards 104, 106 and includes help button or switch 118 and battery 120. Help button 118 and battery 120 are connected by conductive wiring 122 extending through one lanyard 106 to the circuitry within neck strap 108. Thus, there is at least one dedicated connectivity pathway between pendant 102 and the electronics within neck strap 108. Battery 120 powers sensors 110, 112, microprocessor 114 and transmitter 116 via wiring 122, and alarm signals generated by a press of help button 118 can be transmitted to microprocessor 114 and transmitter 116 via wiring 122. In other embodiments, at least some of the circuitry may be provided in the pendent itself, one embodiment of which is shown in FIG. 2. As shown in FIG. 2, the pendant 200 has a rectangular shape planar and oblate cross-sectional shape, and has an activation button 202 disposed on the front of the pendant 200.

By locating the electronics of necklace 100 (sensors 110, 112, processor 114, transmitter 116) within neck strap 108, more available space for larger or additional batteries is provided within pendant 102 while still maintaining an acceptable weight distribution in necklace 100. This extends the operating life of necklace 100, providing the ability to use components with higher power requirements such as a gyroscope, and providing the ability for more frequent motion measurements and transmissions, such that the activity and motion of the user can be documented in greater detail in a memory of the necklace 100 or of the home console, as described in more detail below.

Long range antenna 124 is embedded within the other lanyard 104. Antenna 124 is connected to RF transmitter 116 to allow for transmission of status and alert signals to the personal emergency reporting system console, which are then conveyed on to the central monitoring station. Antenna 124 may have a monopole design extending from the electronics within neck strap 108 towards pendant 102, a loop design around neck strap 108, or a dipole design. By embedding antenna 124 within lanyard 104, a longer antenna may be deployed. Alternatively, or in addition, lanyard 104 may be used to provide an additional wiring pathway between pendant 102 and the electronics within neck strap 108.

Breakaway safety clasp 126 is provided between lanyard 104 and pendant 108 as a safety feature to prevent the possibility of strangulation. Safety clasp 126 is preferably located on the lanyard-side containing the antenna in order to avoid breaking the electrical connection between the electronics within pendant 102 and neck strap 108. By positioning safety clasp 126 near pendant 102, greater user comfort is provided as compared to conventional designs where clasp 126 is located near the neck region.

Connectors 128 of clasp 126 may include a conductive material such as copper such that, where a wiring pathway is provided within lanyard 104, a continuous electrical circuit is formed between all components of necklace 100. By creating a continuous electrical circuit within the necklace, an alarm may be automatically triggered in the event that the safety clasp becomes detached. During dramatic events, such as a fall, the necklace may become separated at the safety clasp due to the violent nature of the event, and perhaps thrown out of range of the user. Also, during such an event where the clasp is separated, the user may be unconscious, injured or otherwise unable to manually signal an emergency alert by pressing help button 118. Automatic alarm triggering eliminates or reduces this problem.

Necklace 100 may also include biometric sensors such as body temperature, pulse rate, oxygen saturation level, blood pressure and other types of sensors embedded in neck strap 108 in order to gather biometric data from the user, and/or contacts in neck strap 108 or a sensor in pendant 102 in order to determine whether necklace 100 is being worn. Alerts may be generated based on predetermined biometric data thresholds or measurements made by the biometric sensors. In some embodiments, the alerts may be based on a generic biometric thresholds such as a predetermined, blood pressure or body temperature. In some embodiments, the alerts may be personalized based on historical biometric thresholds of the user. As above with respect to the fall determination algorithm, while in some embodiments the alert generation algorithm may be attuned to the specific biometric data of the user and programmed into necklace 100 and may operate in collaboration with orientation, acceleration and/or shock threshold. The biometric data may be generated from a previous personal emergency reporting system device associated with the user and stored in a local or remote storage device or a training session with the user when the personal emergency reporting system device is initially obtained. The type of alert may be predetermined based on a particular biometric threshold being reached and, like the algorithm, may be personalized such that the same type of biometric threshold being reached on different necklaces (personal emergency reporting system devices) may provide different types of alerts (e.g., audible/visual/tactile, notifications, etc. . . . ).

By providing two (or more in other embodiments) sensor locations on opposing sides of the neck region or near the upper region of the collar bone, a superior design for motion sensing is provided as compared to a single sensor. Use of two sensors 110, 112 configured in this fashion more accurately captures subtle shifts in the body during normal human movement, such as walking, as weight is transferred from one side of the body to the other. A network of more than one sensor in more than one location on the necklace increases accuracy in the development of comprehensive movement profiles, including the ability to compare and contrast movement patterns, thresholds, orientation and/or other such profiles with different susceptibilities and influences to normal and abnormal body movements. The fixed positions of these multiple data points can be leveraged relative to the orientation or distance of each and/or relative to the normal worn position of the necklace (and as such, relative to the body of the user).

The development of a historical user profile that indicates user activities and effects on sensors 110, 112 may permit necklace 100 to better determine situations in light of the external environment. The effects on sensors 110, 112 may include changes in user biometrics and physical changes to necklace 100, such as orientation. Necklace 100 interacts with the user profile to determine whether a potential fall event is likely a fall event or is part of a normal routine. For example, after being woken up, the sensors in necklace 100 may determine the orientation of necklace 100 has changed from an initial orientation (say vertical) to horizontal or near horizontal or to an inclined position for an extended period and may determine from the user profile that the time of day is night (say 11 PM). The user profile may indicate that the user typically gets into bed and sleeps between around 10:00 PM and 6:00 AM, and thus the orientation of necklace 100 during this time period is considered normal for this user. In addition, the user biometrics may show a steady reduction in heartrate that is consistent with falling asleep, further indicating that this is normal and no alert is to be issued. In this case, necklace 100 may avoid triggering an alert. In other situations, however, the same actions may trigger an alert. Similarly, the profile may indicate to necklace 100 that the user is engaged in an activity such as yoga or is at a regularly scheduled physician appointment, allowing necklace 100 to determine that no alert is needed.

Note that although necklace 100 is referred to herein as having the intelligence as to whether or not to trigger an alert, this decision making may instead be performed at a central monitoring station or home console, as indicated below. This is to say that in such embodiments, necklace 100 may automatically trigger the alert (based on biometrics and physical and the remote equipment may access the user profile and make an automatic determination as to whether or not to further notify rescue services or an emergency contact and/or whether to deactivate any audible/visual alert associated with (e.g., on or near) necklace 100. The user profile may also be used to determine a range of normal rate of change of orientation and acceleration for the user, as determined by one of the sensors, and whether the rate of changed detected exceeds either a predetermined value or a historical rate of change for that user, and subsequently react accordingly such as by waking up the orientation sensor to take one or more orientation measurements. The use of the sensor data, in addition to a user profile, may also permit necklace 100 to be able to determine whether a different user is wearing the device. In some embodiments, multiple user profiles may be stored for different users who may wear necklace 100. The user may signal to necklace 100 that the user has changed via a control such as a button or switch on necklace 100, by making a predetermined controlled gesture with necklace 100, or by accessing necklace 100 or a remote device in communication with necklace 100 and indicating that the alternate user profile is to be used.

In some embodiments, necklace 100 may be able to interact with nearby personal emergency response or other personal electronic devices to determine whether an alert (or limited alert) is to be used. This interaction may be direct, via device-to-device, or may employ the remote equipment. For example, if necklace 100 detects several personal emergency reporting system devices within near communication range (e.g., Bluetooth range), necklace 100 may modify the normal alert behavior by either avoiding transmitting an audible or visual alert or electronic notification (e.g., message or phone call) or by transmitting a truncated alert or notification. Necklace 100, or the network equipment, may modify these actions by determining that others wearing similar personal emergency reporting system devices are likely to be able to notice the fall and take appropriate action.

Although two sensor positions may be used, in another embodiment, only a single sensor position (e.g., where one or more of an accelerometer, gyroscope, magnetometer, altimeter or combinations thereof on a chip) may be located in neck strap 108. The use of a single sensor position in the upper region of necklace 100 is still superior for motion sensing and fall detection as compared to designs that locate the sensor in the pendant. Use of an altimeter, for example, creates advantages by being placed higher on the body, thereby resulting in a greater height differential between both a standing and fallen position and a sitting and fallen position. This allows fall events to be more accurately detected, as compared to designs that locate the altimeter in the pendant 102 (i.e., the lower portion of necklace 100).

Similarly, more than two sensor positions may be used in another embodiment. The sensors may be placed symmetrically or equally around necklace 100. The sensors may all be active at the same time, providing a greater sensitivity at the expense of increased battery drain, or one or more of the sensors may act as a backup if one or more others of the sensors fails, activating only in such a situation.

Figure 3:
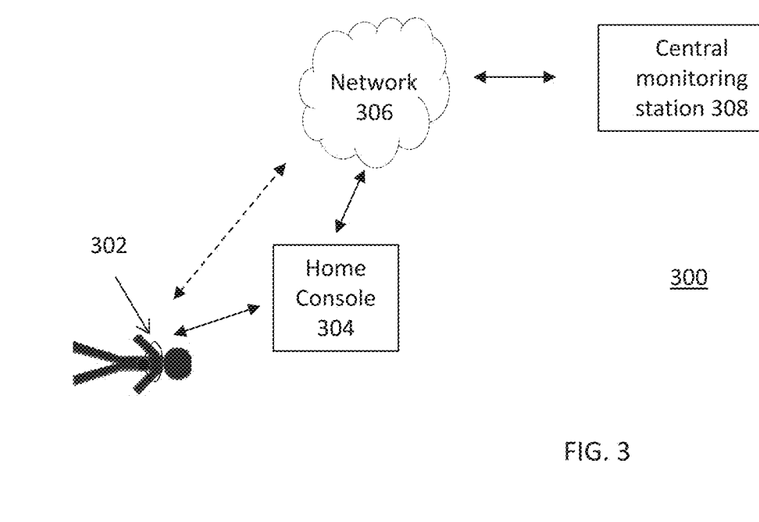
FIG. 3 illustrates a personal emergency reporting system in accordance with some embodiments.

FIG. 3 illustrates one embodiment of a system 300 in which the personal emergency reporting system is used. The system 300 may incorporate some or all aspects of U.S. Pat. No. 8,933,801, entitled "Fall Detection System and Method," which is herein incorporated by reference in its entirety. The personal emergency reporting system device 302 activates when the personal emergency reporting system device 302 detects that the wearer has suffered a fall. The personal emergency reporting system device 302 sends an alert to the home console 304, if located within communication range of the home console 304. The personal emergency reporting system device 302 may communicate with the home console 304 using WiFi, Bluetooth, Zigbee, infrared (IR), near field communication (NFC), 3rd Generation Partnership Project (3GPP) network or other technologies.

The personal emergency reporting system device 302 may transmit fall detection event alerts and motion detection signals, along with environmental information such as time/date and user location (if the personal emergency reporting system device 302 uses global positioning system (GPS), assisted-GPS, localization through access point determination, or other localization techniques) to the home console 304. The home console 304 may store the information before relaying the information through the network 306 to a central monitoring station 308 remote from the home console 304.

The network 306 may be an external network, such as the internet or a private network. Other equipment, such as base stations, routers, access points, gateways and the like used in communicating through the network 306 are not shown for convenience. The transmission through the network 306 may be encrypted or clear. In some cases, the data may be communicated between the home console 304 and the central monitoring station 308 using a virtual private network or other tunneling mechanism.

In some circumstances, the personal emergency reporting system device 302 may transmit the same event information as that to the home console 304 or different information directly to the central monitoring station 308. For example, the different event information may include personal emergency reporting system device ID to the home console 304 and personal emergency reporting system device ID and event type to the central monitoring station 308. The direct transmission may be in addition to, or instead of the transmission to the home console 304, e.g., if the personal emergency reporting system device 302 is unable to communicate with the home console 304. There may thus be a priority system for communication—e.g., attempting communication with the home console 304 a predetermined number of times prior to attempting direct communication with the central monitoring station 308. In some embodiments, the number of times may be dependent on the severity of event as determined by the personal emergency reporting system device 302 via changes in the physical characteristics of the personal emergency reporting system device 302 and/or biometric data of the user determined by the personal emergency reporting system device 302. The personal emergency reporting system device 302 may supplement or update information from the home console 304 such as biometric data and/or device location. Although not shown, the personal emergency reporting system device 302 may also communicate with the home console 304 and/or the central monitoring station 308 through other, nearby personal emergency reporting system device devices with which it is electronically connected. The other personal emergency reporting system devices may in turn relay the information to the home console 304 and/or the central monitoring station 308.

As above, the configuration of the personal emergency reporting system in a necklace that permits extended battery life provides the ability for an increased number of measurements and transmissions. In one embodiment, the personal emergency reporting system device periodically samples the orientation of the personal emergency reporting system device and creates a history of orientation readings during a period of time. The time period may be predetermined or may adjust itself dependent on previous measurements, for example. The personal emergency reporting system device may remain in idle mode until either manually activated (e.g., by pressing the button shown in FIG. 2), an event occurs as detected by the accelerometer or via a shock threshold being exceeded or a counter in the personal emergency reporting system device reaches a predetermined time, say 4 minutes (after which the counter is reset). After waking up, the rate of orientation (and perhaps biometric) measurement taken by the personal emergency reporting system device may vary dependent on the manner by which the personal emergency reporting system device was woken up. For example, the rate may be higher for an event-triggered wake up than for a counter-triggered wake up. Similarly, a manually-triggered wake up may engender a measurement rate higher than a counter-triggered wake up but lower than an event-triggered wake up.

The personal emergency reporting system device may store the orientation history in internal memory and/or communicate the orientation history to the home console. The personal emergency reporting system device may immediately transmit an orientation measurement to the home console or may store the orientation history in internal memory for a predetermined period before communicating the orientation history to the home console, independent of whether an event occurs or at the time an event is determined to occur. In the above example in which an orientation is taken every 4 minutes, in one embodiment, statistics from the 15 readings each hour are sent from the personal emergency reporting system device to the home console using a supervisory transmission every 2 hours. The home console, in turn, may communicate the statistics at regular intervals to the central monitoring station and/or to a cloud server for presentation and access by designated friends and family.

personal emergency reporting system device The amount of time may be predetermined and unable to be altered or may adjust itself dependent on, for example, previous history, time, location and other factors. For example, if the personal emergency reporting system device detects a fall event, the amount of time between at least some of the various measurements may be shortened, whereas if the personal emergency reporting system device determines that the wearer is in bed (e.g., due to user profile and orientation, time and/or location), the personal emergency reporting system device may increase the amount of time between measurements. In some embodiments, after a fall event, the measurement rate for, say, biometrics may increase while for orientation may decrease as the personal emergency reporting system device may determine that biometric measurements are of increased importance. In some embodiments, factors such as the season may be taken into account, as for example, falls or rapid changes in orientation may be more likely during the winter than in the summer. The personal emergency reporting system device, the home console and/or central monitoring system may process the orientation measurements and adjust the fall detection algorithm accordingly as described below.

In some embodiments, individual adjacent or sets of adjacent orientation measurements are compared to extrapolate the change in orientation over time and thus determine the state of movement of the personal emergency reporting system device. Normal variations in the orientation of the personal emergency reporting system device (e.g., those less than the threshold) may indicate activity or movement. The number of orientation measurements as well as the time period over which the orientation measurements are taken may be adjustable. In some embodiments, the orientation measurement comparison is used instead of (or supplementary to) acceleration data or actual movement readings. In the former case, this may decrease the number of components and/or processing power used by the personal emergency reporting system device in determining movement of the personal emergency reporting system device and whether the wearer has taken a fall. In the latter case, the supplementary data may serve to decrease the number of false positive determinations and thus false alerts being transmitted. In some embodiments, changes in orientation and acceleration may be used to adjust the functionality of the personal emergency reporting system device.

As above, a change in the orientation between adjacent orientation measurements that meets or exceeds a predetermined threshold may signify an abrupt action in the part of the individual that is used to determine the probability of the occurrence of a fall and trigger either or both a determination of a fall event occurrence and a more active measurement state of the personal emergency reporting system device for a predetermined amount of time (e.g., 30-60 seconds) to monitor the following changes in orientation and/or changes in biometrics of the user. In some embodiments, to save power the personal emergency reporting system device may not measure biometrics of the user until an event is determined to occur based on the orientation change (and perhaps using an altitude change), or the rate of measurement of the biometrics may increase immediately after the determination of an event (e.g., from 1x/minute to 10x/minute). Instead of a single change in orientation between successive orientation measurements triggering the more active measurement state, multiple changes in orientation that exceed the threshold in sets of successive orientation measurements may trigger the more active measurement state. The thresholds may be different dependent on the axis and the amount of change. For example, a single threshold change may be 60 degrees, while a multiple threshold change may be 30 degrees. This is to say that a change in orientation of more than 60 degrees between successive orientation measurements may trigger the more active measurement state. While a single change in orientation of 30-40 degrees may not trigger the more active state, a change in orientation of 30-40 degrees followed by another change of similar magnitude in successive orientation measurements may, however, trigger the more active measurement state. Similarly, multiple smaller changes in orientation may be used to trigger the more active measurement state. The conditioning of the increased active measurement state on event detection reduces power consumption for activity monitoring by waiting for changes in orientation or taking and comparing spaced measurements of the orientation compared to constant or periodic movement tracking measurements involving the movement of the device for a duration of time.

In some embodiments, changes in orientation from one orientation to another that triggers the more active measurement state and back to near the original orientation (that is back to a "normal") state may reset the personal emergency reporting system device to a default measurement state or an intermediate measurement state that takes a reduced number of measurements compared to the active measurement state but more measurements than the default measurement state. Thus, subsequent motion detection may be used to alter whether or not a fall event has taken place or alert is to be transmitted.

The reset or reduction may occur immediately upon the condition being satisfied or may occur after a predetermined further number of orientation measurements being taken. As above, historical data and/or applied algorithms may be used to supplement the data interpretation and decision making such that the number of false positive fall determinations and alerts is reduced. For example, if the historical data indicates that at certain days and times or location, the orientation is likely to shift radically, such as at a gym or physical therapy, the thresholds may be changed to indicate a wider range of normal variation. Similarly, the thresholds may be changed if historically the wearer is known to be in the company of one or more individuals, thereby reducing the probability of a fall event requiring independent aid or intervention.

In some embodiments, the algorithm may recognize that little or no change in the orientation for a vertical or near vertical position indicates periods of inactivity, such as the wearer being in a sitting or standing position. Similarly, the algorithm may recognize that little or no change in the orientation for a horizontal or near horizontal orientation indicates other periods of inactivity, such as the wearer being in a reclining or sleeping position. An indication of the personal emergency reporting system device being in a horizontal or near horizontal position for an extended period of time during the day with minimal change in orientation outside of the range of the user profile may be an indication of a problem, such as sickness, unscheduled napping, and dizziness and may trigger an alert. If there is no or little movement following a radical movement event, the home console may audibly broadcast an intent to transmit an alarm event and provide an opportunity for the user to cancel the alarm via either the personal emergency reporting system device (e.g., depressing the button on the personal emergency reporting system device) or manually activating a cancellation actuator on the home console.

In some embodiments, if absolutely no change is detected over an extended period of time, such as a day, the algorithm may recognize that the personal emergency reporting system device has been removed even if biometric data is not taken. Once a period of inactivity has been determined, the personal emergency reporting system device may adjust the time period to reduce the number of samples taken. Moreover, the schedule of the wearer may be downloaded to or programmed in the home console and long periods of inactivity over a predetermined time period (e.g., 10:00 pm to 6:00 am) may be considered normal for a particular wearer and thus not result in an alarm being triggered. In some embodiments, the schedule may be linked to a computer, smartphone or other electronic device such that the home console and personal emergency reporting system device automatically adjusts the algorithm (e.g., period, threshold). Note that in some embodiments, updating of the algorithm, fall detection and activity monitoring may be activated and deactivated remotely, depending on the seller/manufacturer/operator and or the owner of the personal emergency reporting system device.

The orientation sensed of the personal emergency reporting system device may have incremental orientation thresholds for measurement and/or triggering different levels of alerts or the orientation thresholds may be substantially continuous. The incremental thresholds may be, for example, 5°, 10°, 30° or 45° increments, among others, while to be substantially continuous the threshold increments may be less than 1° increments. In some embodiments, the orientation increments may change with changing orientation, for example, starting at a larger value and then decreasing with increasing change in orientation to a different value. For example, the initial increment may be 10° and then, once a change of 30° is reached, the increment may change to 5°, where it remains (until being reset by reaching the initial orientation or being reset manually). In another embodiment, multiple decreasing orientation thresholds may be used with increasing orientation change, such as 10° until a change of 20° is reached, 5° from then until 30° is reached, and finally 2°. In some embodiments, the rate of change of threshold may continuously decrease with increasing change in orientation from the initial orientation. This may be useful to counter false alarms associated with normal movement, such as stretching or sneezing, dependent on the type of personal emergency reporting system device. In fact, the orientation increment may depend on the type of personal emergency reporting system device (e.g., worn on the wrist, ankle or around the neck, or dependent on the shape). A personal emergency reporting system device worn on the wrist, for example, may be less sensitive to orientation than one worn on the neck due to the increased likelihood of orientation adjustment.

The orientation determination may, in some embodiments, be in three dimensions or may be limited to one or two dimensions. For example, a wrist-mounted or ankle-mounted personal emergency reporting system device may be sensitive to orientation changes in only two dimensions, ignoring rotational orientation—alternatively, such a personal emergency reporting system device may be orientation-sensitive only if the orientation in the limited direction exceeds a predetermined threshold (e.g., wrist/ankle rotation over 180°). In such embodiments, the personal emergency reporting system device may still measure the rotation but take no action such as alerting, unless the personal emergency reporting system device reaches the threshold.

In some embodiments, a 3-axis accelerometer in the personal emergency reporting system device may be used to set a first G-force threshold to wake up a processor in the personal emergency reporting system device. In some embodiments, the accelerometer may have an output for each axis or one output for the entire accelerometer. The values provided from one or more of the outputs, which may be binary or take other values, may be used for a purpose other than direct computation. In some embodiments, the axes may have thresholds that are independently set to provide a particular output. In some embodiments, the axes may have thresholds that are dependent on each other to provide a particular output. For example, each axis may have to be within the range of ±0.4 G for an output pin of the accelerometer to go high. This range may correspond to a body starting to fall (in which freefall is 0 G).

In some embodiments, rather than process the output from the output pin and determine a resulting value, in response to the processor detecting that the output pin has gone high (or low), the processor may merely activate a 3-axis gyroscope and collect rotational data for several seconds. The rotational data may then be analyzed by the processor or transmitted to an external entity for processing to determine whether there is a correlation to characteristics of an event that would cause the wearer to need assistance (e.g. fell down).

Figure 4:
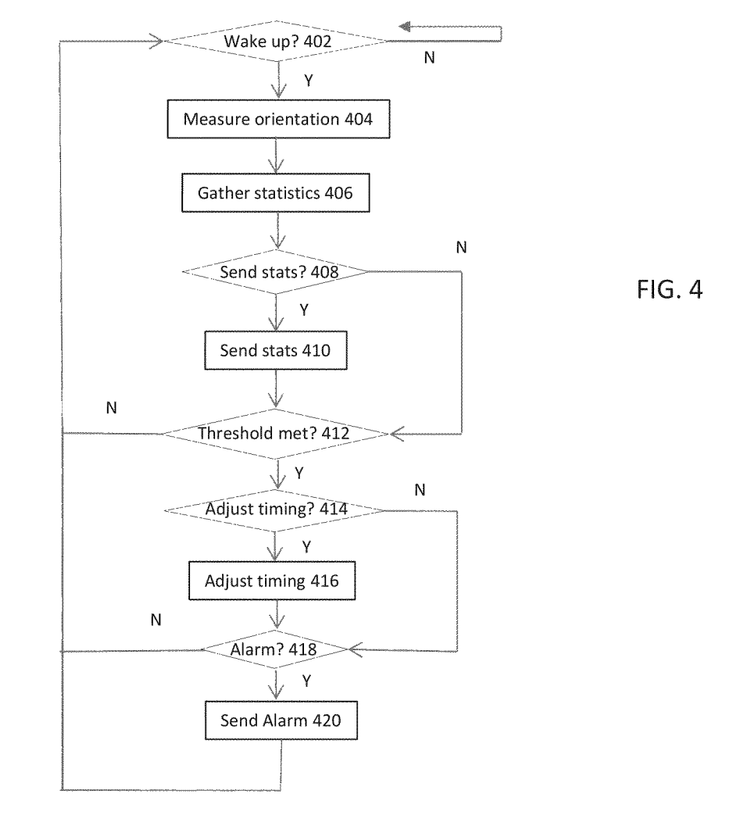
FIG. 4 illustrates a flowchart of a method of using a personal emergency reporting system in accordance with some embodiments.

FIG. 4 illustrates a flowchart of a method of using a personal emergency reporting system in accordance with some embodiments. Note that the various operations may be in a different order than shown and some steps may be eliminated in different embodiments. In operation 402, the personal emergency reporting system device determines whether it is to wake up. This decision may be made on purely timing aspects, manual activation or the accelerometer detecting an abnormal condition.

In operation 404, once the personal emergency reporting system device has woken up, the personal emergency reporting system device measures the orientation of the personal emergency reporting system device. In operation 406, the present orientation of the personal emergency reporting system device is combined with previous orientation measurements to determine orientation statistics. The personal emergency reporting system device next determines in operation 408 whether it has obtained a sufficient number of measurements to send the statistics to the home console and/or cloud server and, if so, transmits the statistics to the appropriate entity at operation 410.

At operation 412, the personal emergency reporting system device next determines whether one of the above predetermined thresholds has been met for changes in orientation. If not, the personal emergency reporting system device returns to idle mode to wait for the next time to wake up and take an orientation measurement. If so, the personal emergency reporting system device determines at operation 414 whether to adjust the timing of how often to take orientation (and perhaps other) measurements. The personal emergency reporting system device may also be able to take physical measurements, such as heartrate and blood pressure, which may be triggered by the threshold being met.

At operation 418, the personal emergency reporting system device determines based on the orientation measurements, statistics and/or physical measurements, among others, whether to transmit an alarm to the home console and/or the cloud. If not, the personal emergency reporting system device returns to idle mode to wait for the next time to wake up and take an orientation measurement. If so, at step 420 the personal emergency reporting system device transmits the alarm, which is relayed to the central monitoring station for the appropriate action to be taken.

The personal emergency reporting system device is thus able to act as a data output device to the home console and cloud. Moreover, in one embodiment the personal emergency reporting system device is able to determine an event (such as a fall) from a short period of significant deviation from the normal movement pattern of the wearer followed by a period of inactivity rather than from an accelerometer-based fall detector measuring acceleration and shock. This is to say that accelerometer measurements alone may, in some embodiments, not be used to determine an event. In one embodiment, the personal emergency reporting system device may be used for data capture and transmission and not (or in addition to) fall determination.

The personal emergency reporting system device in one embodiment may be able to determine through activity monitoring whether the personal emergency reporting system device is being worn. The personal emergency reporting system device may also be able to be used to detect deviations from normal activity levels due to possible health related issues (strokes, seizures, sick spells, fatigue, etc.) allowing for intervention by a caregiver.

Although the above has primarily been discussed for elderly and disabled individuals, the personal emergency reporting system device may also be used for discharged patients and individuals with medical conditions of such a physical or mental state where this technology would be deemed beneficial to their security and well-being. It may be used in residential, assisted living, and hospital conditions. It may also be used for monitoring athletes and animals, both domestic and livestock.

Although an embodiment has been described with reference to specific example embodiments, it will be evident that various modifications and changes may be made to these embodiments without departing from the broader spirit and scope of the present disclosure. Accordingly, the specification and drawings are to be regarded in an illustrative rather than a restrictive sense. The accompanying drawings that form a part hereof show, by way of illustration, and not of limitation, specific embodiments in which the subject matter may be practiced. The embodiments illustrated are described in sufficient detail to enable those skilled in the art to practice the teachings disclosed herein. Some embodiments may be utilized and derived therefrom, such that structural and logical substitutions and changes may be made without departing from the scope of this disclosure. This Detailed Description, therefore, is not to be taken in a limiting sense, and the scope of various embodiments is defined only by the appended claims, along with the full range of equivalents to which such claims are entitled.

Such embodiments of the inventive subject matter may be referred to herein, individually and/or collectively, by the term "invention" merely for convenience and without intending to voluntarily limit the scope of this application to any single invention or inventive concept if more than one is in fact disclosed. Thus, although specific embodiments have been illustrated and described herein, it should be appreciated that any arrangement calculated to achieve the same purpose may be substituted for the specific embodiments shown. This disclosure is intended to cover any and all adaptations or variations of various embodiments. Combinations of the above embodiments, and embodiments not specifically described herein, will be apparent to those of skill in the art upon reviewing the above description.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, UE, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The Abstract of the Disclosure is provided to comply with 37 C.F.R. §1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separate embodiment.

What is claimed is:

1. A personal emergency reporting system (PERS) device comprising:
    an orientation sensor configured to measure orientation of the PERS device;
    a transceiver;
    processing circuitry configured to:
        initiate an orientation measurement based on at least one of timing, manual activation or a sensor detecting an abnormal condition,
        receive from the orientation sensor an orientation measurement,
        determine that a predetermined orientation change in a predetermined time has been met,
        in response to a determination that the predetermined orientation change in the predetermined time has been met, determine whether at least one of:
            a fall event has occurred in response to a determination that each of multiple successive changes in orientation between adjacent orientation measurements at least meets a different predetermined threshold, the predetermined thresholds decreasing with increasing change in orientation from an initial orientation, or
            to enter a more active monitoring state, and
        in response to a determination that a fall event has occurred, instruct the transceiver to transmit an alert signal to at least one of a local or remote device, the alert signal indicating that a fall event has occurred; and
    a housing retaining the sensor, transceiver and processing circuitry and configured to be worn by a user.

2. The PERS device of claim 1, further comprising:
    a plurality of sensors including an accelerometer configured to measure acceleration and shock thresholds, wherein the initiation of the orientation measurement is further based on at least one of the acceleration exceeding a predetermined acceleration or a shock threshold being exceeded, and the determination of whether a fall event has occurred is free from being based on measurements of the accelerometer.

3. The PERS device of claim 1, further comprising:
    a necklace having a neck strap and a pendant connected with the neck strap, and an altimeter disposed in the neck strap, the altimeter configured to measure a change in altitude of the housing, wherein at least one of the initiation of the orientation measurement or the determination of whether a fall event has occurred is further based on a predetermined rate of change of altitude being exceeded.

4. The PERS device of claim 1, further comprising:
a biometric sensor configured to measure biometrics of the user,
wherein a fall detection algorithm stored in a memory of the PERS device is personalized to the user based on historical biometric thresholds of the user.

5. The PERS device of claim 4, wherein:
the historical biometric thresholds one of originate from another PERS device associated with the user or are determined by a training session with the user.

6. The PERS device of claim 4, wherein:
the processing circuitry is configured to determine that a change in orientation between adjacent orientation measurements at least meets another predetermined threshold and, in response, trigger a more active measurement state for at least one of orientation or biometrics for a predetermined amount of time.

7. The PERS device of claim 1, further comprising:
a memory configured to store a historical user profile that indicates user activities, timing of the user activities and effects of the user activities on one or more sensors,
wherein a fall detection algorithm stored in the memory is personalized to the user based on the historical user profile.

8. The PERS device of claim 7, wherein:
multiple users are associated with the PERS device and the processing circuitry is configured to determine, using at least one of the user profile, biometric history or a user-actuated control on the housing, which of the users is wearing the PERS device.

9. The PERS device of claim 1, wherein:
the processing circuitry is configured to determine that another PERS device is proximate and in response adjust transmission of the alert signal to avoid transmitting the alert signal or to transmit a modified alert signal.

10. The PERS device of claim 1, wherein:
the orientation sensor is configured to periodically sample an orientation of the PERS device,
an orientation history is stored in a memory, and
the transceiver is configured to transmit the stored orientation history either periodically or at event-driven times in which a periodicity of transmission is dependent on previous history, and current time and location of the PERS device.

11. The PERS device of claim 1, wherein:
the PERS device is orientation-sensitive in one dimension only when a change in the orientation in the at least one direction exceeds a predetermined threshold.

12. A method of managing a fall event, the method comprising:
measuring orientation of a personal emergency reporting system (PERS) device worn by a user;
determining that a fall event has occurred using at least one orientation measurement to determine that a predetermined orientation change has been met, the fall event determined without using an acceleration measurement;
in response to determining that a fall event has occurred, transmitting an alert signal indicating that a fall event has occurred to at least one of a local device via a short range communication protocol or a remote device via a network communication protocol; and
transmitting orientation history either periodically or at event-driven times in which a periodicity of a transmission of the orientation history is dependent on at least one of previous history, or current time or location of the PERS device.

13. The method of claim 12, further comprising:
initiating the measuring of the orientation based on the acceleration measurement exceeding a predetermined acceleration.

14. The method of claim 12, further comprising:
prior to determining that a fall event has occurred and subsequent to determining that the predetermined orientation change has been met, entering a more active monitoring state in which orientation is measured more frequently than prior to determining that the predetermined orientation change has been met,
wherein determining that a fall event has occurred is dependent on orientation measurements taken during the more active monitoring state.

15. The method of claim 14, further comprising:
measuring biometrics of the user; and
personalizing a fall detection algorithm based on historical biometric thresholds, the historical biometric thresholds of the user being one of transferred from another PERS device associated with the user or determined by a training session with the user,
wherein when in the more active monitoring state, biometric measurements are taken more frequently than prior to entering the more active monitoring state.

16. The method of claim 12, further comprising:
measuring an altitude change, the fall event determination further based on a predetermined altitude change being exceeded.

17. The method of claim 12, further comprising:
personalizing a fall detection algorithm based on a historical user profile that indicates user activities, timing of the user activities and effects on one or more sensors, and determining, using at least one of the user profile, biometric history or a user-actuated control, which of multiple users associated with the PERS device is wearing the PERS device and adjusting the user profile and biometric history accordingly.

18. The method of claim 12, further comprising:
determining that a fall event has occurred in response to determining that multiple successive changes in orientation between adjacent orientation measurements at least meets predetermined thresholds that decrease with increasing change in orientation from an initial orientation.

19. A personal emergency reporting system (PERS) device comprising:
an orientation sensor configured to measure orientation of the PERS device;
a transceiver;
processing circuitry configured to:
initiate an orientation measurement based on at least one of timing, manual activation or a sensor detecting an abnormal condition,
receive from the orientation sensor an orientation measurement,
determine that a predetermined orientation change in a predetermined time has been met,
in response to a determination that the predetermined orientation change in the predetermined time has been met, determine whether at least one of:
a fall event has occurred, or
to enter a more active monitoring state, in response to a determination that a fall event has occurred, determine whether another PERS device is proximate, and
in response to a determination that the other PERS device is not proximate, instruct the transceiver to transmit an alert signal to at least one of a local or remote device, the alert signal indicating that a fall event has occurred, and
in response to a determination that the other PERS device is proximate, adjust transmission of the alert signal to avoid transmitting the alert signal or to transmit a modified alert signal; and
a housing retaining the sensor, transceiver and processing circuitry and configured to be worn by a user.

20. The PERS device of claim 19, further comprising:
a memory configured to store a historical user profile that indicates user activities, timing of the user activities and effects of the user activities on one or more sensors, wherein a fall detection algorithm stored in the memory is personalized to the user based on the historical user profile,
wherein multiple users are associated with the PERS device and the processing circuitry is configured to determine, using at least one of the user profile, biometric history or a user-actuated control on the housing, which of the users is wearing the PERS device.

* * * * *

UNITED STATES PATENT AND TRADEMARK OFFICE
CERTIFICATE OF CORRECTION

PATENT NO. : 9,734,690 B2  
APPLICATION NO. : 15/130405  
DATED : August 15, 2017  
INVENTOR(S) : Haflinger et al.

Page 1 of 1

It is certified that error appears in the above-identified patent and that said Letters Patent is hereby corrected as shown below:

On the Title Page

In item (73), in "Assignee", in Column 1, Line 1, delete "Controls" and insert --Control-- therefor Signed and Sealed this
Twenty-eighth Day of May, 2019

Andrei Iancu
*Director of the United States Patent and Trademark Office*